United States Patent [19]

Jones

[11] Patent Number: 5,368,024
[45] Date of Patent: Nov. 29, 1994

[54] ENDO-TRACHEAL TUBE SECURING SYSTEM

[76] Inventor: Hedi E. Jones, 2243 Westwood Ct., Pittsburg, Calif. 94565

[21] Appl. No.: 93,878
[22] Filed: Jul. 20, 1993
[51] Int. Cl.⁵ .................. A62B 9/06; A61M 16/00
[52] U.S. Cl. .................. 128/207.17; 128/200.26; 128/207.14; 128/DIG. 26
[58] Field of Search .......... 128/207.17, 207.18, 128/207.15, 200.26, 911, 207.14, 204.18, DIG. 26, 912, 206.25, 201.14, 201.19, 201.24; 2/9, 206; 24/265 BC, 265 R, 172, 182; 433/5

[56] References Cited

U.S. PATENT DOCUMENTS

| | | | |
|---|---|---|---|
| 2,898,917 | 8/1959 | Wallace | 128/DIG. 26 |
| 3,976,080 | 8/1976 | Bornhorst et al. | 128/DIG. 26 |
| 4,191,180 | 3/1980 | Colley et al. | 128/207.17 |
| 4,351,331 | 9/1982 | Gereg | 128/207.17 |
| 4,480,639 | 11/1984 | Peterson et al. | 128/207.17 |
| 4,660,555 | 4/1987 | Payton | 128/DIG. 26 |
| 4,988,291 | 6/1991 | Grummons | 433/5 |

Primary Examiner—Edgar S. Burr
Assistant Examiner—William J. Deane, Jr.

[57] ABSTRACT

A securing system for an endo-tracheal tube in which a holder in the shape of an open ring with side-flanges is slipped around the tube. Adhesive discs bearing catches are stuck to the patient's face in front of the ear lobes with bands securing the ring flanges to the catches. Additional bands run to and from the remaining catches over the patient's head and around his neck to provide counterpull.

5 Claims, 1 Drawing Sheet

U.S. Patent
Nov. 29, 1994
5,368,024
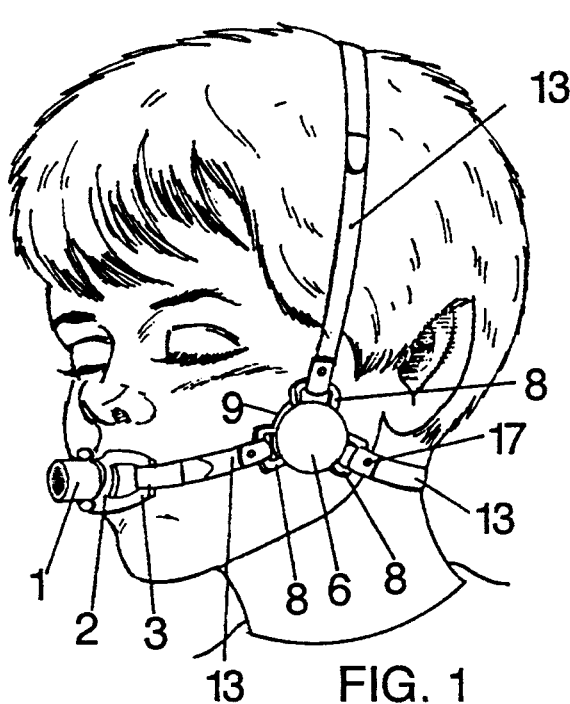
FIG. 1
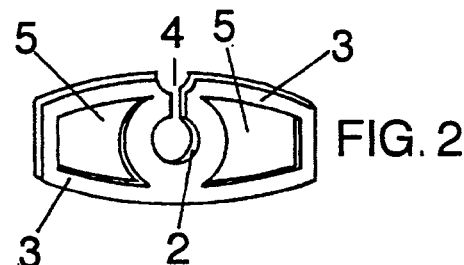
FIG. 2
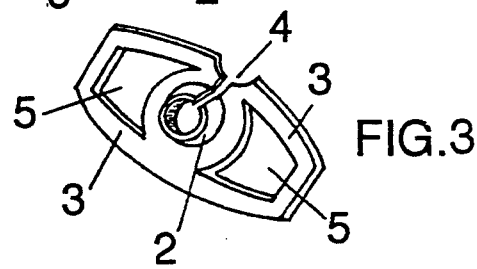
FIG. 3
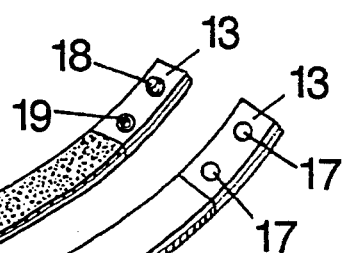
FIG. 4
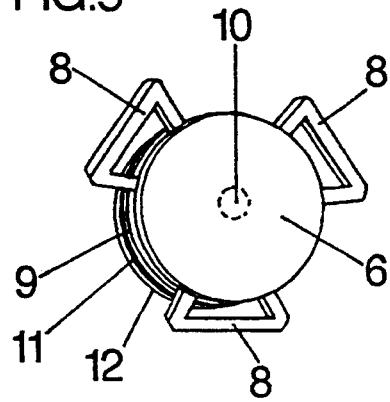
FIG. 5
FIG. 6
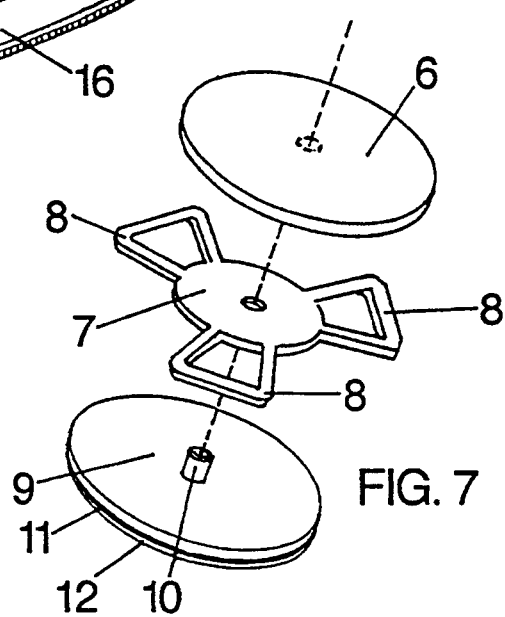
FIG. 7

ENDO-TRACHEAL TUBE SECURING SYSTEM

BACKGROUND OF THE INVENTION

1. Field of the Invention

The invention relates generally to a system to secure an endo-tracheal tube after the patient is intubated and hold it in the patient's mouth and throat so that it will not dislodge. It consists of a tube holder, two disc assemblies which adhere to the patient's face having three catches each, and bands to connect the holder to the catches on either side. The system is further secured by bands around the patient's head.

2. Description of the Prior Art

Endo-tracheal tubes are inserted into an unconscious patient's trachea through the mouth to open an airway. Securing the tube after insertion is very important, because if it is dislodged accidentally or coughed out, it could mean the patient's life. But securing the tube adequately has always been problematical. At present this is done with adhesive tape which is wound around the tube and then stuck to the patient's face and neck. This is not satisfactory for long-term use, since the tape is constantly exposed to moisture from the mouth and loses it's adhesive quality. Yet some anchoring to the face is essential, since any other method does not provide sufficient security for the tube. Bands or cord alone will slip and are too risky to use by themselves. It is the object of this invention to provide a securing system which eliminates adhesive tape and the problems occasioned by it, yet assures safety for the tube by using a combination tying and anchoring method.

SUMMARY OF THE INVENTION

The invention consists of a tube holder in the form of an open ring which snaps around the endo-tracheal tube with a snug fit. Shield shaped flanges defining an open space on both sides of the ring provide attaching means for bands. Two disc assemblies which can be anchored to the face in front of each ear lobe by means of adhesive provide three catches each. One catch on each side will receive the bands which are attached to the tube holder flanges. The other two catches will be secured to the corresponding one on the other side by bands which will run over the top of the patient's head and around his neck respectively. The bands are rubberized on the underside to prevent them from slipping.

BRIEF DESCRIPTION OF THE DRAWINGS

FIG. 1 shows the invention in use in an intubated patient. The disc assembly is attached to the patient's face in front of the ear lobe. The tube holder is snapped around the endo-tracheal tube and is secured to the disc assembly with bands as shown, providing three-way pull.

FIG. 2 shows the tube holder in a front perspective view. The central ring which is open at the top snaps around the tube, the side flanges provide attaching means for bands.

FIG. 3 shows the tube holder in a back perspective view. This shows the protruding portion of the ring which stabilizes the tube.

FIG. 4 is a top view of a band, showing VELCRO and snap button closures on either end.

FIG. 5 is a bottom view of a band, showing a rubberized surface to provide cling to the skin.

FIG. 6 is a perspective view of the disc assembly showing three rigid loops which form catches for the band.

FIG. 7 is a detailed view of the disc assembly, showing the top and bottom disc joined by a central stem and the revolving middle disc bearing the three catches.

DESCRIPTION OF THE PREFERRED EMBODIMENT

Referring to FIG. 1, an embodiment of the invention is shown. The endotracheal tube 1 is in the patient's mouth and throat. To keep the tube 1 in place, a holder in the shape of an open ring 2 and made of rigid plastic is snapped around the tube 1. The endo-tracheal tube 1 is slightly flexible and can be depressed and pushed through the opening 4 in the ring 2. When inside the ring 2, the tube 1 will resume it's shape and fill the ring 2 with a tight fit, being stabilized by it. The ring 2 has shield-shaped flanges 3 defining an open space 5 on both sides, following the curve of the mouth. The ends of the flanges 3 form bars around which holding bands 13 are looped. A disc assembly consisting of two discs 6 and 9 is attached to the patient's face in front of the ear lobe on both sides by means of an adhesive layer 11 on the bottom disc 9. Between the discs 6 and 9 which are joined by a central stem 10 sits a revolving wheel 7 with three equidistant catches 8 for the attachment of the holding bands 13. Two of the bands 13 run from the holder flanges 3 to the nearest catch 8 on either side. The remaining two bands 13 are attached to the second and third catch 8 on either side, running over the patient's head and behind his neck respectively and providing counterpull. In this way the pull on the tube 1 is distributed three ways and the distribution point being anchored to the face, the possibility of the system slipping or the tube 1 becoming dislodged is eliminated.

Referring to FIG. 2, the tube holder 2 is shown in detail. The opening 4 in the ring 2 is rounded on top to facilitate the sliding in of the tube 1. The slightly curved flanges 3 provide stability for the ring 2 and a means of attachment for the holding bands 13. Both holder ring 2 and flanges 3 are made of rigid plastic in one integral piece.

Referring to FIG. 3, a back view of the holder 2 is shown. The ring 2 protrudes somewhat towards the back to provide better support for the tube 1.

Referring to FIG. 4, one of the holding bands 13 is shown from the front. The top of the band 13 has a loop closing surface 14, except for the tip, which is of hook closure 15, so that the band 13 can be closed upon itself.

Referring to FIG. 5, one of the holding bands 13 is shown from the back. The back of the band 13 has a rubberized surface 16, which enables the band 13 to cling to the patient's skin without slipping. In order to attach the band 13 to the catch 8, a set of male and female snap buttons 18 and 19 is provided for each band 13 which can snap upon itself after being looped through the catch 8. Then only the back of the snap buttons 17 will show.

Referring to FIG. 6, one of the two disc assemblies made of rigid plastic is shown. It consists of a top disc 6 which is integrally joined to a bottom disc 9 by a central stem 10. Revolving around the central stem 10 is a wheel 7, bearing three equidistant catches 8, which extend beyond the rim of the discs 6 and 9, and form holding bars for the bands 13. The bottom disc 9 has an adhesive layer 11 on its outer surface, so that it can be attached to the patient's face. When not in use, the adhesive layer 11 is protected by a peel-off cover 12.

Referring to FIG. 7, the disc assembly of FIG. 6 is shown in greater detail. Here the wheel 7 is visible as lifted off the central stem 10 around which it revolves. This is necessary so that the disc 9 can be attached to the patient's face without regard to which way the catches 8 will be pointing. By revolving the wheel 7 slightly, the catches 8 can be made to face in-the proper direction.

Although an embodiment of the invention is illustrated in the drawings and is previously described in detail, this invention encompasses also any configuration, design or relationship of components which will function in a similar manner and which will produce the equivalent results. For instance this securing system could be modified to work for naso-gastric tubes or eye protectors.

I claim:

1. An endo-tracheal tube securing system comprising:
   (a) an endo-tracheal tube holder in the shape of an open ring having on both sides slightly curved flanges defining an open space and forming attaching means, said holder being made of a rigid material in one integral piece;
   (b) a disc assembly made of a rigid material comprising two discs and a central stem joining said discs, a wheel bearing three equidistant catches extending beyond the rim of the discs to provide attachment means, said wheel revolving around said stem, an adhesive layer on the outer surface of one of said discs the whole disc assembly being capable of attachment to a patient's face by means of said adhesive layer and a protective peel-off cover for said adhesive layer when not in use;
   (c) four holding bands of varying length, two of which connect the holder flanges to the catches, the remaining two bands securing the remaining catches to each other over and around the patient's head.

2. An endo-tracheal tube securing system as recited in claim 1, in which the opening in the holder ring permits an endo-tracheal tube to be squeezed therethrough, the inner diameter of the ring corresponding to the outer diameter of the endo-tracheal tube to provide a snug fit.

3. An endo-tracheal tube securing system as recited in claim 2, in which the curved flanges are attached to the front of the ring and form a continuous surface with the rim of the ring and leave a portion of the ring to protrude giving more support to the tube.

4. An endo-tracheal tube securing system as recited in claim 3, in which the holding bands are made of fabric with the upper surface having loop closing means and a tip of hook closing means, allowing the band to be closed upon itself and the lower surface being rubberized to provide cling for the skin.

5. An endo-tracheal tube securing system as recited in claim 4, in which one end of the holding bands has a set of snap buttons, so that the bands can be secured around the catches.

* * * * *